United States Patent

Miljkovic

[11] Patent Number: 5,962,049
[45] Date of Patent: Oct. 5, 1999

[54] BORON CARBOHYDRATE COMPLEXES AND USES THEREOF

[76] Inventor: Dusan Miljkovic, 4351 Nobel Dr., #62, San Diego, Calif. 92122

[21] Appl. No.: 09/045,141

[22] Filed: Mar. 20, 1998

Related U.S. Application Data

[60] Provisional application No. 60/042,883, Mar. 31, 1997.

[51] Int. Cl.$^6$ .............................. A23L 1/30; A23L 1/304
[52] U.S. Cl. ............................................. 426/74; 426/658
[58] Field of Search ..................................... 426/74, 658

[56] References Cited

U.S. PATENT DOCUMENTS 3,821,196   6/1974   Arthur, Jr. et al. ..................... 260/212

OTHER PUBLICATIONS van den Berg et al., Carb. Res., vol. 253, pp. 1–12, 1994.
Verchere et al., Polyhedron, vol. 6(6), pp. 1415–1420, 1987.
Conner, J. Inorg. Nucl. Chem., vol. 32, pp. 1545–1548, 1970.
Aruga, J. Chem Soc, Dalton Trans., pp. 2971–2974, 1988.
Hu et al., Plant Physiol., vol. 113, pp. 649–655, 1997.

*Primary Examiner*—Chhaya D. Sayala
*Attorney, Agent, or Firm*—Robert D. Fish; Crockett & Fish

[57] ABSTRACT

Complexes of boron with sugars or/and sugar alcohols are utilized as nutritional supplements, with the carbohydrate portion being selected to provide a relatively high boron-sugar association constant of at least 250, and preferably 500 or more. In one class of preferred embodiments, boron is complexed with a saccharide having co-planar cis-OH groups capable of forming five or six membered rings through ester bonding with boric acid. Such complexes may advantageously comprise fructose, mannose, xylose or sorbose. In another aspect of the invention, a carbohydrate-boric acid complex may be charge neutralized with calcium, magnesium or other cation(s). A particularly preferred form is calcium fructoborate. In yet another aspect of preferred embodiments, the boron supplement can be included in a food, especially in a high magnesium food, and more especially in a snack food such as a snack containing chocolate and/or nuts.

20 Claims, 1 Drawing Sheet

BORON CARBOHYDRATE COMPLEXES AND USES THEREOF

This application claims priority to provisional application serial no. 60/042,883 filed Mar. 31, 1997.

FIELD OF THE INVENTION

The field of the invention is dietary boron.

BACKGROUND OF THE INVENTION

There is an absolute requirement for boron in many plants. In vascular plants, for example, boron is essential for the structure and function of cell walls, and may also be important in regulating hormones. In many animals, boron apparently also plays an important role, especially in calcium and magnesium metabolism. In chickens, for example, boron deficiency leads to poor growth and leg abnormalities in chicks, while boron supplementation produces stronger egg shells. (Mastromatto E., et al., "Summary: International Symposium on the Health Effects of Boron and its Compounds", *Environ Health Perspect.*, 1994 November; 102, 7:139–41).

In humans boron offers significant benefits with respect to bone and joint health. Supplemental boron has also been shown to improve mental functions such as eye-hand coordination, attention, perception, short-term and long-term memory, and likely promotes healthy hair, skin and nails. (McCoy et al, *Environ. Health Persepct.*, 1994 November; 102 Suppl. 7:49–53; U.S. Pat. No. 5,312,816 to Spievogel et al., issued May 17, 1994; "Newnham, *Environ. Health Perspect.*, 1994 November; 102 Suppl., 7: 8305; Penland, J. G., *Environ. Health Perspect.*, 1994 November; 102 Suppl., 7:65–72; Murray, T., H., "Keep bones and joints healthy with boron", *Health Counselor*, 1997 June–July, 32–33.

The optimum daily intake of boron in humans appears to be about 2–3 mg/day. The bioavailability of boron in both water and foods is relatively high, and in theory this optimum daily intake could be readily obtained from a high quality diet. In water, for example, about 89% of boron is absorbed, and in foods such as broccoli absorption may reach 100%. Unfortunately, however, this amount is not present in ordinary diets, as the dietary intake of boron by individuals in North America is reported to be only about 1 mg. It also turns out that boron is most helpful when magnesium levels are sufficient, and magnesium levels are notoriously deficient in modern diets.

Supplemental boron is known in many different forms. As over-the-counter supplements, for example, boron is marketed as calcium borogluconate (Now Foods, Glendale Hts., Ill.), and as boron citrate, aspartate and glycinate chelates (Twin Laboratories, Inc., Ronkonkoma, N.Y.). U.S. Pat. No. 4,849,220 to Hunt, issued Jul. 18, 1989, describes the addition of boric acid ($H_3BO_3$) to the diet of postmenopausal women, and U.S. Pat. No. 5,312,816 to Spielvogel et al. describes dietary supplementation with Lewis-acid base boron adducts. Boron has also been given as a simple salt, such as sodium borate, or sodium tetraborate decahydrate.

These known forms of boron supplementation leave something to be desired. First, the known forms either contain or are readily hydrolyzed in the gut to boric acid. Boric acid is reactive, and tends to accumulate in tissues other than bone or joint. Second, the amount of boron made available by known supplementation is extremely high compared with normal blood values. A typical boron supplement, for example, may make almost 3 mg of elemental boron available to the tissues within a half hour after ingestion, which is about 14 times the normal total blood boron of 213 $\mu$g. (Hunt, C. D., et al., "RDA Workshop: New Approaches, Endpoints and Paradigms for RDAs of Mineral Elements", *American Institute of Nutrition*, 1996, pp 2441S–2451 S). Third, while there is a mechanism which limits boron absorption from foods when boron intake is high, (Hunt, C. D., et al., "RDA Workshop . . . ", supra), that mechanism likely does not act to prevent the almost immediate availability of boron from currently known supplements. Fourth, it has been estimated that less than a quarter of the population takes vitamin/mineral supplements on a daily basis, so that the known forms of supplementation are unlikely to reach a high percentage of the population.

Thus, there is a continuing need to provide boron in a supplementation form in which the elemental boron is tightly bound to a ligand. Since blood boron levels are probably transiently defined by a single meal, and highly influenced by snacks, there is also a need to provide boron in conjunction with a food which is commonly eaten, preferably on a relatively frequent basis such as in a snack. Still further, there is a need to provide boron in conjunction with a source of magnesium.

SUMMARY OF THE INVENTION

In the present invention complexes of boron with sugars and/or sugar alcohols are utilized as nutritional supplements, with the carbohydrate portion being selected to provide a boron-sugar association constant of at least 250, and preferably 500 or more.

In one class of preferred embodiments, boron is complexed with a saccharide having co-planar cis-OH groups capable of forming five or six membered rings through ester bonding with boric acid. Such complexes may advantageously comprise fructose, mannose, xylose or sorbose. In another aspect of the invention, a carbohydrate-boric acid complex may be charge neutralized with calcium, magnesium, manganese, iron, copper, zinc, chromium, vanadium or other cation(s). A particularly preferred form is calcium fructoborate.

In another aspect of preferred embodiments, the boron supplement can be included in a food. Essentially the entire gamut of foods are contemplated, including both solid and liquid foods, staples and snacks, and highly processed and minimally processed foods. Particularly preferred foods are magnesium containing foods, and especially magnesium containing snack foods such as those containing chocolate and/or nuts.

In still another aspect of preferred embodiments, a sugar-boron compound as described herein can be utilized as an ingredient in a pharmaceutical preparation.

Various objects, features, aspects and advantages of the present invention will become more apparent from the following detailed description of preferred embodiments of the invention, along with the accompanying drawing.

DETAILED DESCRIPTION

Figure 1:
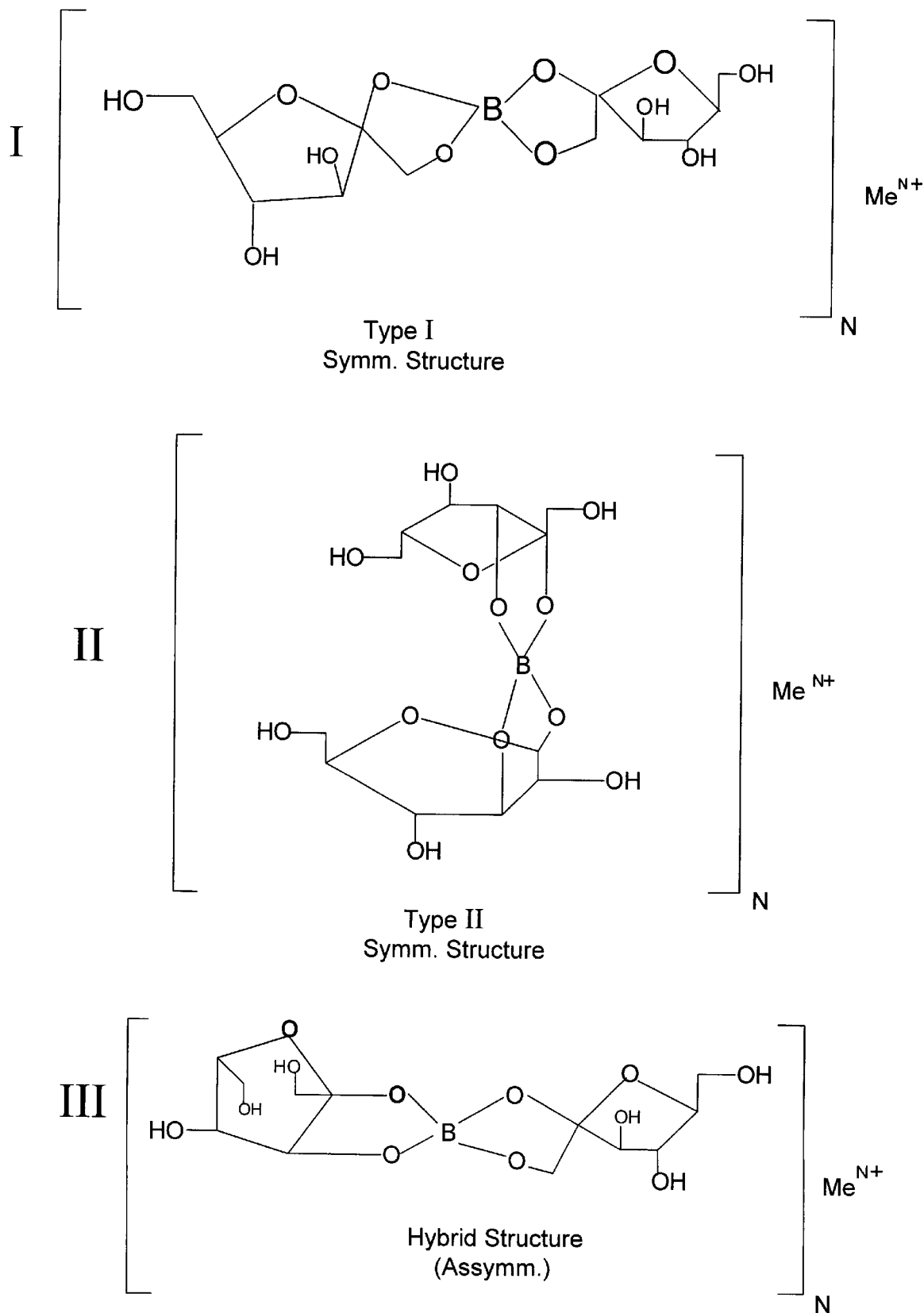
FIG. 1 is a schematic showing three contemplated structures I, II and III according to one aspect of the present invention, wherein $Me^{n+}$ comprises a metal ion having a valence of n+.

The present invention contemplates the use of sugar-boron complexes as nutritional supplements. Since boron may be best handled by the body in small doses spread throughout the day, it is preferred that such boron supplements would be included in foods, and especially in foods such as snacks which may be consumed throughout the day. While not limiting the class to particular types of snacks, it is contemplated that boron supplements according to the present invention may be included in solid snacks such as candies, cookies, crackers and chips, and also in beverages including soft drinks, juices, milk, liquor, beer wine and other spirits. Liquids in general may, in fact, be particularly desirable carriers for boron supplements because they may facilitate distribution of the supplement. In addition to snack foods, boron supplements according to the present invention may advantageously be included in staple foods such as cereals or rice, and other foods such as pet foods, TV dinners and so forth. In all of these and other instances, the term "included in" is intended to broadly encompass situations in which the boron supplement is added to the food before, during or after other processing, and where the supplement is added using whatever means is available.

Still further, it is contemplated that since boron is most helpful where adequate magnesium is present, preferred boron supplemented foods may also contain relatively high amounts of magnesium. Particularly high magnesium containing foods are nuts, especially almonds (over 350 mg/oz), and chocolate (over 80 mg/oz.). For these reasons sugar-boron supplements may advantageously be added to chocolate and chocolate nut bars, chocolate syrups, and so-called "breakfast bars" or "snack bars" at up to 3 mg of boron per serving. Other preferred foods are those containing at least 25 mg/oz of magnesium, and more preferably at least 50 mg/oz of magnesium.

Of course, completing of sugar-boron supplements with other cations is also contemplated, including especially other cations having nutritional value such as manganese, iron, copper, zinc, chromium, and vanadium.

Sugar-boron compositions employed according to the present invention can be prepared in any suitable manner. In an exemplary synthesis, calcium fructoborate can be prepared by providing an aqueous fructose solution, adding boric acid to produce a fructose-borate solution, and then adding calcium carbonate to produce calcium fructoborate. In many cases these reactions will proceed spontaneously, and almost totally to completion. The sugar borate solution, for example, is considerably more acidic than boric acid itself, and readily displaces the carbonate. The calcium salt can then easily be crystallized. Where the starting sugar mixture contains both glucose and fructose, for example, the D-Glucose can be almost completely regenerated from the mother liquor. If desired, the crystalline fructose complex may then be purified further by recrystalization, or by other suitable means. As in many syntheses, it is contemplated that the final product will be present as an equilibrium of several different forms. It is contemplated, for example, that a fructoborate such as calcium fructoborate will be present in at least the three forms depicted in FIG. 1, with the equilibrium concentration of II being much greater than III, which in turn is greater than 1.

In alternative syntheses, it is contemplated that the solvent may comprise water, ethanol, acetone or any other appropriate, and preferably amphiphilic solvent. It is also contemplated that the starting sugar mixture may comprise any sugar or combination of sugars. Suitable sugars for the reaction thus include mono- di-, tri-, oligo- or polysaccharides, and may range from small three carbon sugars to the larger pentoses, hexoses and so forth. It is still further contemplated that calcium carbonate can be replaced or supplemented with another metal carbonates, such as Mg carbonate.

Not all sugars, however, are equally preferred. As mentioned above, it may be desirable for human and animal nutrition to provide sugar-boron complexes in which the association constant between boron and the carbohydrate ligand is relatively high. The association constants for boron and a single sugar ligand, (i.e., B-L), were characterized for many sugars are set forth in van den Berg, et al., "The structure and (local) stability constants of borate esters of mono- and di-saccharides by $^{11}$B and $^{13}$C NMR spectroscopy", *Carbohydrate Research*, 1994, 253: 1–12, from which the following is abstracted:

| | |
|---|---:|
| α-Maltose | 3 |
| α-Lactose | 15 |
| α-Glucopyranose | ≈0 |
| β-Isomaltulose | 2,500 |
| β-Turanopyrnaose | 250 |
| β-Arabinofuranose | 6,000 |
| β-Fructofuranose | 6,000 |
| β-Fructopyranose | 500 |
| α-Galactofuranose | 3,500 |
| β-Lactulofuranose | 4,500 |
| β-Sorobofuranose | 40,000 |
| α-Xylofuranose | >16,000 |
| α-Tagatopyranose | 1,500 |
| β-Tagatopyranose | 10,000 |

Without relying on this particular data, or on the validity of any particular theory in the interpretation of the appended claims, it is contemplated from this listing that relatively high association constants with boron arise from co-planar cis-OH groups capable of forming five or six membered rings through ester bonding with boric acid. From this relationship it is contemplated that preferred sugar-boron supplements are those in which the sugar has a favorable diol configuration, or an equivalent configuration. In terms of B-L association constant, preferred supplements are those in which the B-L association constant is at least 250. In more preferred embodiments the supplement may have a B-L association constant of at least 500, 1000, 2,500, 5,000 and in particularly preferred embodiments the B-L association constant will be at least 10,000. Thus, boron complexes with sorbose or xylose are greatly preferred. In another aspect, however, it is also desirable to provide nutritional supplements which utilize especially common and well tolerated sugars, such as fructose, which also have a relatively high association constant.

From the above discussion it is also contemplated that both sugar (keto- and aldo- forms) and sugar alcohols will be suitable for inclusion in nutritional supplements. Thus, boric acid compounds of sorbose, sorbulose, sorbitol, and xylose, xylulose, and xylitol are all contemplated In terms of furanose and pyranose forms, it is contemplated that one or both forms may be suitable, depending upon the sugar. In many cases the distinction is somewhat moot in any event, because one form or the other greatly predominates in any solution.

The boron contemplated to be used herein may predominantly comprise any mixture of the two naturally occurring forms of boron, namely $^{10}$B and $^{11}$B. In nature, these elements are present in about a 4:1 ratio, and it is contemplated that the ratio of boron in preferred supplements herein will have substantially the same ratio.

Preferred supplementation of foods with sugar-boron complexes is contemplated to provide at least 0.1 mg of boron per serving, and less than about 3–5 mg boron per day. More preferred sugar-boron complexes may provide at least 0.5 mg of boron per serving. At these levels, foods containing the contemplated sugar-boron compounds are expected to be completely safe. Complexes with two mannitol or sorbitol ligands complexed to a single borate center are naturally present in celery, radishes, peaches and other foods. Penn, S. G., et al., "Direct Analysis of Sugar Alcohol Borate Complexes in Plant Extracts by Matrix-Assisted Laser Desorption/Ionization Fourier Transform Mass Spectrometry", *Anal. Chem.*, (1997) 69: 2471–2477; Hu, H. et al., "Isolation and Characterization of soluble boron Complexes in Higher Plants", (1997) 113: 649–655.

On the other hand, it is contemplated that the various sugar acids such as gluconic acid would not be particularly suitable because of their unfavorable configurations and consequently low association constants. In any event, the terms "sugars" and "sugar alcohols" are contemplated herein to exclude sugar acids. These terms also exclude amino acids and other polyhydroxy acids such as citric acid and malic acid.

In still other aspects, it is contemplated that preferred sugar-boron complexes may be complexed with a cation to form a salt. Thus, FIG. 1 depicts fructoborate complexed on a 2:1 molar basis with calcium$^{2+}$. Other contemplated cations include ions of calcium, manganese, iron, copper, zinc, chromium, and vanadium.

In still other aspects, it is contemplated that sugar-boron compounds may be included in pharmaceutical preparations either as an active ingredient or an adjunct. Such preparations may be administered in any acceptable route, including per os, sublingually, by injection or intravenous infusion, nasally, by suppository, transcutaneously, and so forth, with suitable excipients, binders, carriers and other compounds included as known in the pharmaceutical arts. Dosage of such preparations is contemplated to provide between about 0.01 mg/day/dose to about 10 mg/day/dose or more of boron.

EXPERIMENTS

General Procedure: A concentrated water or ethanol solution of a carbohydrate (one molar equivalent) is treated with boric acid (one or one half molar equivalent), at room temperature, while stirring. The reaction mixture should be checked for pH (with a pH-meter). Within minutes the pH drops to between 3 and 4, and then one half molar equivalent of solid Ca-carbonate is introduced in small portions to reaction mixture. Stirring is continued for another ten to fifteen minutes, during which time carbon dioxide is evolved. After the evolution of carbon dioxide is ceased, the stirring is stopped and solvent is removed in high vacuum, or the solution is lyophilized. This procedure was checked with D-fructose, D-mannitol, D-altrose, D-altritol, Dgalactose, D-galactitol, maltitol, inulin and some other selected carbohydrates, and in all cases the same general pattern prevailed. Characterization of the crystalline products is best done by performing elemental microanalyses, and taking the corresponding 13-C-NMR spectra preferably in $D_2O$.

Ca-Fructoborate: D-Fructose (2.16 g) is dissolved in water (4 ml) at room temperature. Boric acid (0.372 g) is then added to the thus prepared solution, and upon its dissolving calcium carbonate (0.246 g) is added in small portions. After carbon dioxide evolution has ceased, acetone (99%, p.a. quality; 20 ml) is added to the reaction mixture, whereupon a colorless oil separates at the bottom of the reaction vessel. Two layers are separated using a separatory funnel, and the lower layer (crude boron complex) is treated again with acetone (20 MI). Upon standing at room temperature for one hour, the mixture is triturated using a glass rod to induce crystallization, and the oil slowly solidifies. This produces a white crystalline solid. The solid is filtered off on a Buchner funnel, washed with additional acetone, and air dried. The solid is then further dried in a vacuum oven at room temperature, leaving a solvent free, very pure Ca-fructoborate. The yield is 2.05 g (75%).

Thus, boron containing nutritional supplements have been disclosed, as well as methods of including such supplements in foods. It should be apparent to those skilled in the art, however, that many more modifications besides those already described are possible without departing from the inventive concepts herein. For example, nutritional supplements as contemplated herein need not be included in foods per se, but may be included in vitamin pills or other forms of supplements. The inventive subject matter, therefore, is not to be restricted except in the spirit of the appended claims.

What is claimed is:

1. A method of supplementing boron intake in an individual, comprising:

providing a carbohydrate-boron complex having a boron portion and at least one carbohydrate ligand complexed to the boron portion with a boron-ligand association constant of at least 250; and providing the carbohydrate-boron complex to the individual as a nutritional supplement.

2. The method of claim 1 wherein the association constant is at least 500.

3. The method of claim 1 wherein the association constant is at least 1,000.

4. The method of claim 1 wherein the association constant is at least 5,000.

5. The method of claim 4 wherein the carbohydrate is selected from the group consisting of mannose and mannitol.

6. The method of claim 4 wherein the carbohydrate is selected from the group consisting of sorbose and sorbitol.

7. The method of claim 1 wherein the association constant is at least 10,000.

8. The method of claim 1 wherein the complex comprises a dietary supplement.

9. The method of claim 1 wherein the carbohydrate portion includes co-planar cis-OH groups capable of forming a ring through ester bonding with boric acid.

10. The method of claim 9 wherein the carbohydrate comprises fructose.

11. The method of any one of claims 1–10 wherein the carbohydrate-boron complex is charge neutralized with a cation.

12. The method of claim 11 wherein the cation is selected from the group consisting of calcium, magnesium, manganese, iron, copper, zinc, chromium, and vanadium.

13. A food containing a complex according to any one of claims 1–10.

14. The food of claim 13 comprising at least 50 mg of magnesium per ounce.

15. The food of claim 13 comprising at least one of chocolate and nuts.

16. A food containing at least 0.1 mg of boron in a supplement according to any one of claims 1–10, wherein the carbohydrate-boron complex is charge neutralized with a cation, and further comprising at least one of chocolate and nuts.

17. The food of claim 16 wherein the carbohydrate-boron complex comprises a calcium fructoborate.

18. A food containing at least 0.5 mg of boron in a supplement according to any one of claims 1–10, wherein the carbohydrate-boron complex is charge neutralized with a cation.

19. A food containing at least 0.5 mg of boron in a supplement according to any one of claims 1–10, wherein the food is selected from the group consisting of a snack, a prepared food, a pet food, a candy, and a beverage.

20. The food of claim 19 wherein the carbohydrate-boron complex is charge neutralized with a cation selected from the group consisting of calcium, magnesium, manganese, iron, copper, zinc, chromium, and vanadium.

* * * * *